| (12) United States Patent | (10) Patent No.: US 7,726,969 B2 |
| Walther | (45) Date of Patent: Jun. 1, 2010 |

(54) DENTAL IMPLANT, IN PARTICULAR OF CERAMIC MATERIAL

(76) Inventor: Gerd Axel Walther, Bahnhofstrasse 18, 71034 Böblingen (DE)

( * ) Notice: Subject to any disclaimer, the term of this patent is extended or adjusted under 35 U.S.C. 154(b) by 125 days.

(21) Appl. No.: 11/957,897

(22) Filed: Dec. 17, 2007

(65) Prior Publication Data

US 2008/0286721 A1 Nov. 20, 2008

(30) Foreign Application Priority Data

May 12, 2007 (EP) .................................. 07009562

(51) Int. Cl.
*A61C 8/00* (2006.01)
(52) U.S. Cl. ...................................... 433/174; 433/175
(58) Field of Classification Search .......... 433/172–176
See application file for complete search history.

(56) References Cited

U.S. PATENT DOCUMENTS

| 5,197,881 | A | | 3/1993 | Chalifoux | |
| 5,437,551 | A | * | 8/1995 | Chalifoux | 433/173 |
| 6,663,389 | B1 | * | 12/2003 | Gallicchio | 433/173 |
| 6,846,180 | B1 | * | 1/2005 | Joos | 433/174 |
| 2005/0202371 | A1 | | 9/2005 | McGuire | |

FOREIGN PATENT DOCUMENTS

| DE | 102005013200 A1 | 9/2006 |
| EP | 0216031 A1 | 1/1987 |
| EP | 19635619 A1 | 3/1998 |
| EP | 0827721 A1 | 11/1998 |
| EP | 00/54696 A1 | 9/2000 |
| EP | 1186275 A1 | 3/2002 |

* cited by examiner

*Primary Examiner*—Ralph A Lewis
*Assistant Examiner*—Eric Rosen
(74) *Attorney, Agent, or Firm*—Browdy and Neimark, PLLC

(57) ABSTRACT

A dental implant including more especially a ceramic material has an implant body for anchoring in a jawbone. An implant post as a tooth support is inserted into the implant body and locked by use of a plug and turn coupling as a bayonet connection.

13 Claims, 3 Drawing Sheets

DENTAL IMPLANT, IN PARTICULAR OF CERAMIC MATERIAL

BACKGROUND OF THE INVENTION

The invention relates to a two-part dental implant, in particular of ceramic material as is for example described in the German patent publication De 10 2005 979 A1.

THE PRIOR ART

In the case of the known dental implant although by suitable shaping the implant post is arranged in a non-rotatable fashion in the implant body, it is not held interlockingly to prevent its being drawn out in the axial direction and is held by means of an adhesive. This is something which is disadvantageous in many cases.

The European patent publication EP 11866257 A1 admittedly discloses a two-part dental implant in which the implant post, termed a connecting body, is screwed into the implant body, but however such a fine female thread is only suitable for metallic dental implants such as those of titanium and is unsuitable for ceramic ones. The manufacture of such fine female threads for ceramic dental implants is technically problematical.

SHORT SUMMARY OF THE INVENTION

One object of the invention is to provide a two-part dental implant, more particularly of ceramic or another non-metallic material, in the case of which the implant post is anchored or able to be anchored and is interlockingly secured in the implant body against being drawn out without a screw thread being necessary.

This object is achieved in accordance with the invention by dental implant having the features of claim 1 herein.

The anchoring in accordance with the invention of the implant post by a bayonet coupling in the form of a plug and turn connection provides an interlocking coupling to prevent pulling out by traction and may be made by a simple plugging and turning operation through an extremely small angle. As compared with a screw thread such a bayonet coupling may be designed to be geometrically coarser and accordingly technologically more simply, more especially in conjunction with two- or multi-part dental implants, which are at least partially manufactured of a ceramic material or of another non-metallic material, in the case of which the application of a female thread is a problem.

The claims define advantageous developments of the invention and also improvements in the invention as recited in claim 1 herein.

The implant post preferably possesses a holding portion able to be plugged into the implant body for anchoring in the implant body and a load carrying portion protruding from the implant body in the inserted state thereof to receive a fixedly secured dental prosthesis, such as a separate crown, bridge column or the like.

In accordance with a particularly preferred design of the bayonet coupling the holding portion of the implant post has a radially protruding locking element arrangement, which is able to be inserted through a complementary structure of the implant body into same and by rotation is able to be locked behind such complementary structure. In this respect the locking element arrangement possesses, in a convenient design, preferably a symmetrically distributed number of locking teeth and the complementary structure possesses one or more corresponding insertion recesses. Accordingly there is then the possibility of a rapid and simple locking of the implant post in the implant body with only a little manufacturing complexity or expense.

The locking element arrangement locked behind the structure is preferably designed in the form of a clamping locking means, i.e. on rotation the locking teeth jam behind the complementary structure. This leads to security as regards unintended rotation. In addition this effect may be achieved in the form of interlocking anti-turn means such that there is a coupling member, which is connected with the anchored and firmly seated dental prosthesis, and has an more particularly conical recess to receive the load bearing portion of the implant post, said coupling member having at least one pin-like projection extending in an axial direction for fitting into the complementary structure of the implant body. This at least one pin-like projection in this case preferably is of a length sufficient for rotationally locking the implant post in the implant body and can also fill and accordingly seal all receiving recesses in the complementary structure.

The holding portion able to be plugged into the implant body of the implant post and the corresponding socket in the implant body is preferably conically tapered in the insertion direction, this facilitating and improving the jamming in place of the coupling member. Accordingly the load bearing portion as well of the implant post is conically tapered toward its free end in order to have a correspondingly better anchoring of the coupling member. As an alternative to a conical geometry other configurations are possible, such as a cylindrical or non-radially symmetrical ones.

For anchoring in the jaw the implant body can possess a male thread, i.e. preferably a conical and/or self-tapping screw thread, with the aid of which the implant body may be screwed into a corresponding hole in the jaw.

In accordance with an advantageous embodiment of the invention the dental implant consists at least in part of a ceramic material on the basis of zirconium oxide or a zirconium oxide/aluminum blend or of another non-metallic material, as for example a fiber reinforced plastic on a carbon fiber basis.

Further advantageous developments and convenient forms of the invention will be understood from the following detailed descriptive disclosure of two embodiments thereof in conjunction with the accompanying drawings.

LIST OF THE SEVERAL VIEWS OF THE FIGURES

DETAILED ACCOUNT OF WORKING EMBODIMENTS OF THE INVENTION

Figure 1:
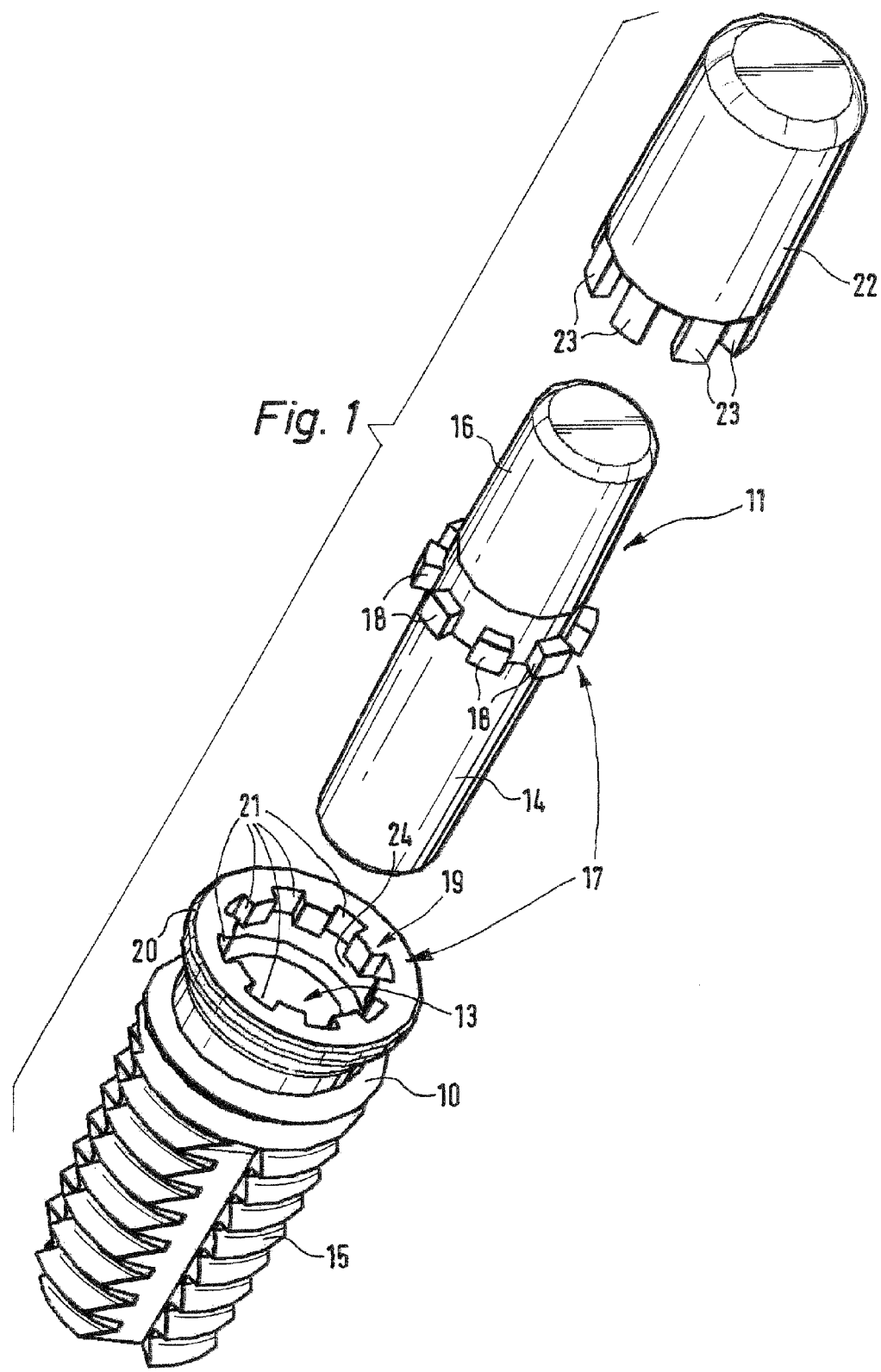
FIG. 1 shows a perspective exploded view of the dental implant comprising an implant body, an implant post and a coupling means as a first embodiment of the invention.

The dental implant represented in the figures as a first working example consists an implant body 10 adapted to be inserted or respectively screwed into the human jawbone, an implant post 11 able to be held in this implant body 10 by detent means and a coupling member 22 adapted to be placed on the post 11 provided with a dental prosthesis (not illustrated) to be anchored to it, such as a separate crown, a bridge column or the like. These components consist partly or entirely of a ceramic material on the basis of zirconium oxide or a zirconium oxide/aluminum oxide blend. The components completely or partially protruding from the jawbone and more especially the implant post 11 and coupling member 22, yet to be described, preferably consist of the ceramic material or another non-metallic material, as for instance a fiber reinforced plastic based on carbon fiber, last but not least for aesthetic reasons and for the sake of appearance, whereas the implant post 10 secured in the jawbone can also comprise a metal, as for example titanium. In principle however the entire dental implant could consist of metal.

The implant body 10 possesses a blind hole 13 tapering conically inwardly to receive a correspondingly tapering holding portion 14 of the implant post 11. Peripherally the implant body 10 is provided with a conical and/or self-tapping male thread 15 serving to screw into the hole in the jaw. Instead of a male thread 15 it is possible in principle for some other known external structure to serve for anchoring in a jawbone.

The holding portion 14 of the implant post 11 is integrally adjoined by a load bearing portion 16, which extends in the implant post, inserted in the implant body 10, from the implant body 10 and serves for holding a firmly seated dental prosthesis. Furthermore the load bearing portion 16 as well tapers toward the free end conically, as is also the case with the holding portion 14. As an alternative to the conical shape other geometries are possible as well, such as a cylindrical or a non-radially symmetrical configuration.

For securing the implant post 11 in the implant body 10 use is made of a plug and turn bayonet coupling 17. For this purpose the implant post 10 exhibits a generally centrally placed ring of radially protruding locking teeth 18 whereas at the open terminal portion of the implant body 10 a complementary structure 19 is arranged on a terminal flange 20 having correspondingly groove-like receiving recesses 21. For a mutual engagement together of the parts the implant post 11 is so introduced into the implant body 10 that the locking teeth 18 are shifted right through the receiving recesses 21 of the complementary structure 19. Then the implant post 11 is rotated through an angle corresponding essentially to the angular width of a locking tooth 18. This means that the locking teeth 18 assume positions behind the complementary structure 19, the conical holding portion 14 being so designed in conjunction with the correspondingly designed blind hole 13 in the implant body 10, the locking teeth 18 and the complementary structure 19 that during such rotation of the locking teeth 18 there is a clamping or bracing action directly behind the complementary structure 19, i.e. the holding portion 14 of the implant post 11 is then thrust into the blind hole 13 and so clamped in place. The annular groove 24 may for example be made helically oblique in accordance with the number of teeth portions so that the implant post 11 on rotation is thrust and jammed in the blind hole 13 and the holding portion 14 is pressed fast and fixed in the blind hole 13. This action can also be enhanced and facilitated if the holding portion 14 and/or the blind hole 13 are provided with a plastic coating.

In the working embodiment I provide eight evenly distributed locking teeth on the periphery of the implant post 11 and there is a corresponding number of receiving recesses 21. This number may, naturally be varied. In the simplest case a single locking tooth 18 and a single receiving recess 21 will suffice. However it is better to have a larger number of locking teeth 18, which should be evenly distributed about the periphery. Furthermore the locking teeth 18, the receiving recesses 21 and the annular groove 24 may also have a configuration departing from the rectangular or cubic shape (or cross section) and f. i. be semicircular, triangular, elliptical or the like in their geometry.

In the working embodiment illustrated the bayonet coupling 17 is arranged on the open end portion of the implant body 10 or, respectively, on the free terminal portion, facing away from the free terminal portion, of the holding portion 14 of the implant post 11. In this case it is in principle possible for the locking teeth 18 to be arranged at a different position on the holding portion 14 so that the bayonet coupling 17 is arranged farther to the inside of the implant body 10.

A cup-like coupling member 22 is provided with a firmly anchored dental prosthesis in a dental lab or such coupling member 22 is seated and anchored, in such dental prosthesis, such as a separate crown, a bridge column or the like. The coupling member 22 provided with the dental prosthesis (not illustrated) is then placed on the conical load bearing portion 16 of the implant post 11 so that such load bearing portion 16 fits into a suitably shaped socket in the coupling member 22. Pin-like projections 23 extend from the edge of the open end of the coupling member 22 in an axial direction and are so shaped and arranged that they may be introduced into the receiving recesses 21 in the complementary structure 19. The length thereof is such that they fit between the locking teeth 18 of the implant post 11 and accordingly prevent turning or turning back of the implant post 11. The implant post 11 thus locked both in the axial direction and also in the direction of turning as well.

In order to produce the locking effect the number of teeth of the pin-like projections 23 could also be less than the number of the receiving recesses 21, although however an equal number and an identical cross sectional configuration is to be preferred so that the implant post 10 is completely terminated and sealed and not foreign matter can find its way into it.

For the attachment or fitting of the dental implant firstly the implant body 10 is screwed in a hole in the jawbone in a known fashion, using the male thread 15, and so anchored in position. Some time prior to the production of the firmly seated dental prosthesis the implant body 10 is then sealed off by the insertion and rotation of the implant post 11, a protective cap being provided if desired as an alternative or in addition. Furthermore a suitably adapted gingival shaper and possibly a provisional structure may be inserted or applied. After the production of the final dental prosthesis, in which the coupling member 22 is anchored, the latter is so fitted on the implant post 11 using the coupling member 22 so that the pin-like projections 23 pass through the receiving recesses 21 and are positioned between the locking teeth 18 in order to lock the implant post 11. The conical load bearing portion 16 of the implant post 11 then comes into intimate contact with the corresponding recess in the coupling member 22, anchoring then being able to take place in a known manner by bonding or with a cement with conventional adhesive materials or however a radial screw or bolt is employed for locking in position. The coupling member 22, which may be mass produced and connected in the lab with the firmly seated dental prosthesis, means that no particular adaptation thereof at the dentist is necessary, since the coupling member 22 is adapted and fettled in an optimum fashion to match the implant post 11.

As a modification of the illustrated working example the implant post may also be angled i.e. the longitudinal axis of its holding portion is set at an angle in relation to the longitudinal axis of its load bearing portion as necessary for adaptation to the setting of the dental prosthesis. In the case of such a design a large number of locking teeth 18 is an advantage in order to be able to undertake the positioning in a more adaptable fashion.

Moreover the load bearing portion of the implant post may also possess a configuration departing from a conical shape and may f. i. be cylindrical or spherical in structure. The corresponding recess in the coupling member must naturally be adapted to such particular shape, additional means possibly being provided to prevent rotation.

Figure 2:
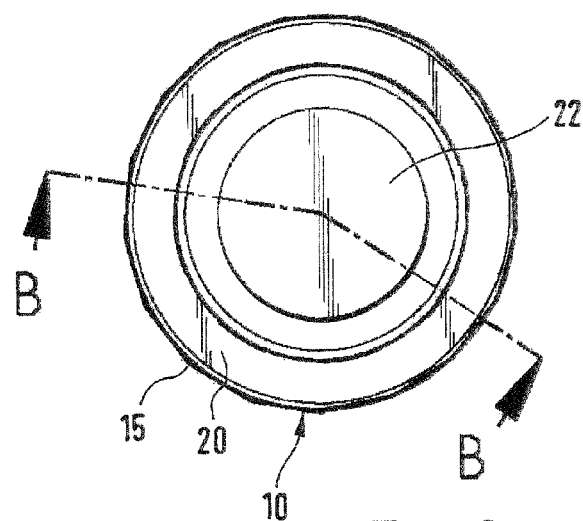
FIG. 2 is a plan view of the dental implant in accordance with FIG. 1.
Figure 3:
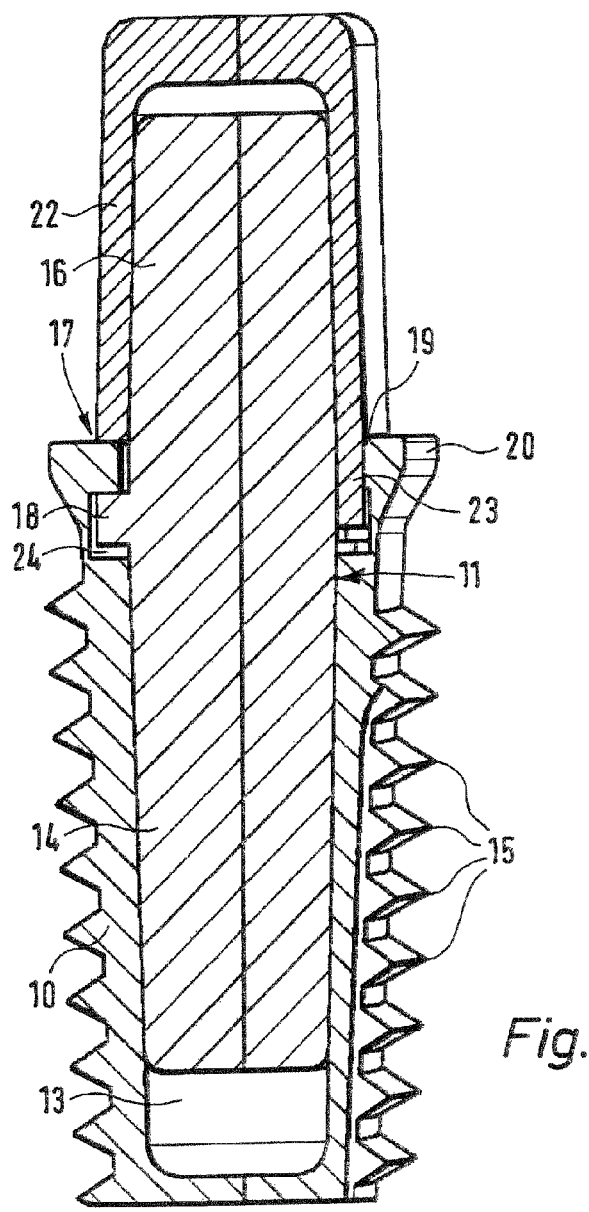
FIG. 3 is a sectional view of the assembled dental implant in accordance with FIG. 1 on the section line B-B.
Figure 4:
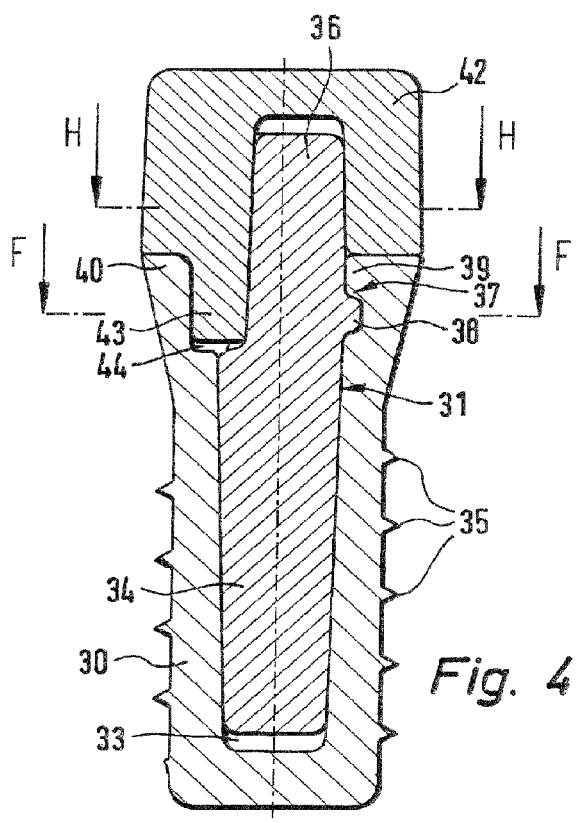
FIG. 4 is a longitudinal representation of an assembled dental implant as a second working example of the invention.
Figure 5:
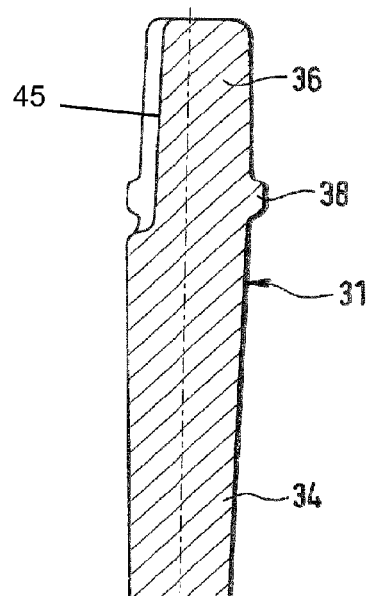
FIG. 5 is a separate view of the implant post in accordance with FIG. 4.
Figure 6:
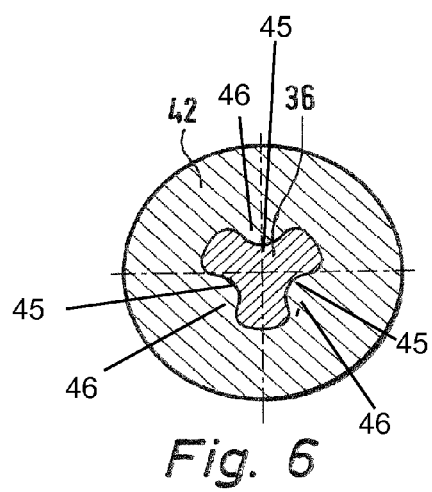
FIG. 6 shows a cross sectional view of the structure of FIG. 4 on the section line H-H.
Figure 7:
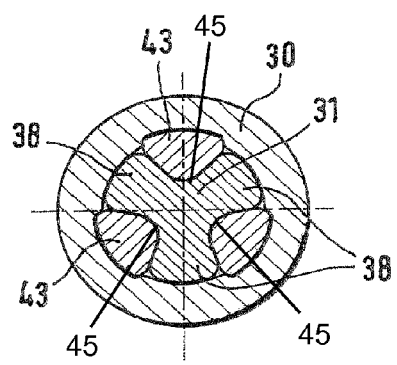
FIG. 7 is a cross sectional view of the structure of FIG. 4 taken on the section line F-F.

In the case of the second embodiment, depicted in FIGS. 4 through 7, functionally corresponding and equivalent means are provided with reference numerals corresponding to the numbers used in FIGS. 1-3 plus 20 and are not described in detail over again. Differing from the first working example the load bearing portion 36 of the implant post 31 possesses third peripherally distributed longitudinal grooves 45 extending in the longitudinal direction, into which, when the coupling member 42 is in place, complementarily designed rail-like lugs 46 on the coupling member 22 fit. Accordingly the implant post 31 may be simply screwed using a suitably shaped tool into the implant body 10 and fixed in position and using such implant post lithe implant body 10 (connected with it) may also be screwed into the jaw. Furthermore owing to this design the wall thickness of the coupling member 42 may be increased and made stronger.

Differing from the first working example the coupling member 42 only possesses three pin-like projections 23 for introduction in the openings in the complementary structure 39, only three locking teeth 38 being possessed by the implant body 30. The terminal flange 40 is made larger than the remaining portion of the implant body 30 in diameter like a ramp and on its free end has the same diameter as the coupling member 42 at this position so that a transition without a ledge is produced.

The locking of the implant post 31 by means of the locking teeth 38 behind the complementary structure 39 of the implant body 10 like a bayonet coupling takes place as in the first working example.

The invention claimed is:

1. A dental implant, in particular of ceramic material, comprising an implant body for anchoring in a jawbone and an implant post as a tooth support, said post being able to be inserted into the implant body and locked therein by means of a bayonet connection as a plug and turn joint,
   wherein the implant post possesses a holding portion adapted to be introduced into the implant body and a load bearing portion projecting from the implant body in the inserted state thereof,
   wherein the holding portion of the implant post has a radially extending locking element arrangement, which is able to be introduced through a complementary structure of the implant body into the same and by rotation is able to be locked behind such complementary structure, and
   further comprising a coupling member joined to a firmly seated dental prosthesis to be anchored, said coupling member having a recess to receive the load bearing portion of the implant post, said coupling member having at least one pin-like projection in the axial direction for fitting into the complementary structure of the implant body.

2. The dental implant as set forth in claim 1, wherein the locking element arrangement possesses at least one symmetrically distributed number of locking teeth and the complementary structure has one or more corresponding receiving recesses.

3. The dental implant as set forth in claim 1, wherein the locking element arrangement locked or able to be locked behind the complementary structure is designed in the form of a clamping locking means, more particularly for jamming the holding portion of the implant post in the implant body.

4. The dental implant as set forth in claim 1, wherein the recess for receiving the load bearing portion is conical in form.

5. The dental implant as set forth in claim 1, wherein the at least one pin-like projection possesses a length sufficient for locking the implant post in the implant body against rotation.

6. The dental implant as set forth in claim 1, wherein one or more of the pin-like projections is or are adapted to fill all receiving recesses of the complementary structure.

7. The dental implant as set forth in claim 1, wherein the holding portion able to be inserted into the implant body of the implant post and a corresponding socket in the implant body are tapered conically in the insertion direction.

8. The dental implant as set forth in claim 1, wherein the load bearing portion of the implant post is conically tapered toward its free end or is shaped cylindrically or spherically.

9. The dental implant as set forth in claim 1, wherein the load bearing portion has a plurality of groove-like wells running in the longitudinal direction to receive correspondingly shaped rail-like lugs on the coupling member.

10. The dental implant as set forth in claim 1, wherein the implant body possesses a male thread and preferably a conical and/or self-tapping male thread.

11. The dental implant as set forth in claim 1, wherein said implant consists completely or partially of a ceramic material on the basis of zirconium oxide or a zirconium oxide/aluminum oxide blend or another non-metallic material.

12. The dental implant as set forth in claim 1, wherein the holding portion of the implant post and/or the corresponding socket of the implant body are coated with plastic.

13. The dental implant as set forth in claim 11, wherein at least the components projecting from the jawbone consisting of the ceramic material or of the non-metallic material.

\* \* \* \* \*